US006857318B1

(12) United States Patent
Silber et al.

(10) Patent No.: US 6,857,318 B1
(45) Date of Patent: Feb. 22, 2005

(54) METHOD FOR THE NON-INVASIVE MEASUREMENT OF AN INTERNAL PRESSURE

(75) Inventors: Gerhard Silber, Frankfurt am Main (DE); Michael Stanull, Obertshausen (DE); Matthias Wackenreuther, Saulheim (DE); Eva-Maria Schuttler, Frankfurt am Main (DE); Jochen Lohberg, Wollstadt (DE)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/980,702

(22) PCT Filed: Apr. 22, 2000

(86) PCT No.: PCT/EP00/03654

§ 371 (c)(1),
(2), (4) Date: May 13, 2002

(87) PCT Pub. No.: WO00/65322

PCT Pub. Date: Nov. 2, 2000

(30) Foreign Application Priority Data

Apr. 26, 1999 (DE) .......................................... 199 18 714

(51) Int. Cl.[7] .............................................. G01L 7/10
(52) U.S. Cl. .................................... 73/730; 73/862.454
(58) Field of Search .................. 73/700–756, 862.454, 73/862.381, 862.391, 862.42, 862.451, 862.471, 862.621

(56) References Cited

U.S. PATENT DOCUMENTS 5,457,999 A * 10/1995 Feldman ...................... 73/704

FOREIGN PATENT DOCUMENTS

| DE | 44 27 991 A1 | 2/1996 |
| DE | 197 18 806 A1 | 5/1998 |
| DE | 197 47 254 A1 | 5/1999 |
| DE | 199 18 714 | 7/2001 |
| EP | 0 501 234 B1 | 9/1992 |

OTHER PUBLICATIONS

English Language Abstract of Germany—197 47 254 A1.
English Language Abstract of Germany—199 18 714.
English Language Abstract of Europe—0 501 234 B1.
English Language Abstract of Germany—197 18 806 A1.
English Language Abstract of Germany—44 27 991 A1.

* cited by examiner

Primary Examiner—Edward Lefkowitz
Assistant Examiner—Jermaine Jenkins
(74) Attorney, Agent, or Firm—Bell Boyd & Lloyd LLC

(57) ABSTRACT

The invention relates to a method for the non-invasive measurement of the internal pressure of elastic vessels, according to which a restoring force is detected on the outer surface of the vessel and the internal pressure is determined from the measured force and the relaxation curve of the vessel. The aim of the invention is to be able to measure internal pressure in a simply yet highly accurate manner. To this end the relaxation curve is determined repeatedly after the start of the measurement.

13 Claims, 5 Drawing Sheets

METHOD FOR THE NON-INVASIVE MEASUREMENT OF AN INTERNAL PRESSURE

This application is a 371 of PCT/EP00/03654 Apr. 22, 2000.

The invention relates to a method for the non-invasive measurement of internal pressure in elastic vessels in which a force is measured on the outer surface of the vessel and the internal pressure is determined by means of a difference of the measured force and a relaxation curve of the vessel estimated in advance.

In a number of applications, it is desirable to determine the internal pressure in a tube or some other vessel without having to establish communication with the interior of the tube. This is especially true in the medical area, where one would like to minimize the danger of infection of a patient by creating as few entrance points for germs as possible. Examples of applications are cleansing of blood in the case of dialysis patients, or the connection of a heart-lung machine.

It is known that many of the materials used for the vessels, especially for tubes, exhibit a creep behavior, so that even in the case of a constant internal pressure a change in the measured force occurs with the passage of time. This simulates a drop in the tube internal pressure.

It was therefore suggested in EP 0 501 234 B1 that the actual measuring time be preceded by a preparation time in which the tube is pre-tensioned in a deforming manner over a rather long time period. In so doing, it is assumed that after this time no more creep events will occur and that the determined signal, namely, the reaction force, will yield correct information about the internal pressure actually prevailing in the tube.

An improved measurement results from a method described in DE 197 47 254 A1, published subsequently. This document begins from the fact that the material will still creep even after a certain time. This behavior, which is also called relaxation behavior, is taken into account by a function for which necessary parameters are determined prior to the measurement. During the measurement, the difference between the measured values and the relaxation function predicted or estimated in advance with the aid of the parameters is then taken into account in order to calculate the actual internal pressure.

The invention is based on the problem of achieving good accuracy in a simple measurement of internal pressure.

This problem is solved in a method of the initially cited type, in that the relaxation curve is repeatedly checked after the start of measurement.

Basically, a prediction about the future behavior of the vessel is made with the relaxation function. According to the invention a check is made after the start of measurement of whether the prediction applies or not. In the latter instance the prediction is corrected so that the relaxation behavior of the vessel can be predicted with greater reliability. It can then be assumed during the further measurement that the difference between the relaxation curve of the vessel and the measured force is all the more accurate the more recently in the past the last prediction of the relaxation curve took place. In addition, there is the fact that over the course of time more and more measured values become available. The more measured values are available, the more accurately the relaxation curve can be replicated. The more accurate the replication, the greater the probability that, at least for the near future, the prediction "is true." A higher degree of accuracy in measuring internal pressure can be achieved in this manner. Since the measured values of the force are available in any case, only a slightly greater effort is required in processing the measured values. However, this effort can be readily accomplished with the processors available today.

Preferably, the relaxation curve is determined with the aid of an averaging method. This is especially advantageous if the internal pressure itself pulses or varies approximately periodically, as is the case, e.g., when using peristaltic pumps or piston pumps to deliver a fluid through the vessel. Detection of the relaxation is then not impossible, but it is difficult on account of the pulsation. This difficulty can be circumvented in a simple manner in that the average or mean value of the measured forces is formed, or the measured values filtered over a predetermined time. The time period during which the average value is formed is carried along as a time window. Thus, the average value also always refers to a time period of a predetermined length prior to the current point in time.

Formation of an average value preferably takes place in at least two different ways, which differ by their smoothing width. For example, a time period is used for the one formation of average value that is twice as long as the time period for the other formation of average value. This yields an improved monitoring and, in particular, errors and disturbances can be recognized more rapidly.

This is especially true when a difference of the average values with a differing smoothing width is formed continuously. An average value formed over a rather long time period reacts more slowly to a change in behavior than an average value formed over a rather short time period. If it is assumed that measurement of the forces takes place in both instances with the same chronological resolution, then it can also be assumed that given a rather large number of measured values, the average value follows the actual curve with a greater sluggishness than in the case of a rather small number of measured values. In an "undisturbed" situation the sluggishness plays no part. The average values will thus substantially coincide. The differences are then in only an admissible tolerance range. If, however, the internal pressure rises sharply, e.g., in the form of a "jump," the two average values with differing smoothing widths will then differ very sharply. Such a jump can then be recognized from this difference.

A periodicity of the measured force is preferably determined and a window width for the formation of average value is coordinated at least from time to time with the periodicity. The periodicity can be determined, e.g., by counting the minima over a certain time period. It can be arranged for formation of average value to take place over a predetermined number of whole periods. This improves the accuracy of the average values. Since it is possible for the periodicity to vary, it can be provided that a predetermined number of average value formations will be performed with the same smoothing length, and the periodicity then re-determined.

A preferred embodiment provides for a first limit to be continuously formed that results from the fact that the relaxation curve drops monotonically, and a second limit is continuously formed that results from the fact that the slope of the relaxation curve decreases, and a change of the internal pressure is recognized if the relaxation curve exceeds one of the two limits. The change of the measured forces can have two causes. For the first, the forces change because of the relaxation behavior of the vessel, and for the other, the measured forces change when the internal pressure changes. This change can occur in different ways. It can be a jump, for example. This change is recognized quite reliably by the difference formation from average values with differing smoothing widths. However, the change can also result from a slowly changing internal pressure, e.g., when an infusion needle slowly becomes clogged. This change can be so small that it only slightly exceeds the changes of measured values occasioned by the relaxation behavior. However, such changes can be recognized in that a "slope triangle" is placed in the relaxation curve and a check is made to see whether the measured values are still within the triangle. It is known of course that the relaxation curve falls monotonically. If, therefore, measured values, or more precisely, the average value from the measure values, rises, then this cannot be explained by the relaxation. Conversely, it is known that the negative slope of the relaxation curve always becomes smaller in amount and thus asymptotically approaches a straight line. If this gradient suddenly becomes greater, this can then not be due to the relaxation behavior of the vessel, but rather tends to indicate a change of internal pressure. Taking these insights into account, processing of the measured forces can then be appropriately controlled.

In order to predict the relaxation curve, support points are preferably repeatedly determined. Processing of individual values, namely, the values at the support points, is substantially simpler than processing of a continuous function with theoretically an infinite number of values. It has even turned out that the information necessary to enable predicting the relaxation curve reliably enough can be gained with a certain number of support points.

The support points are preferably determined in an initializing phase at given points in time, and in a measuring phase after a predetermined change of the predicted relaxation curve. For example, atmospheric pressure is present in the interior of the vessel in the initializing phase. A sufficient number of measured values can now be determined at the support points in a relatively short time because these support points are fixed in time. The relaxation curve can be predicted at least for the near future with the measured values determined. For example, four support points are already sufficient to enable making a first prediction. With six more support points the prediction can be stabilized such that the measuring can be started. However, as time increases the relaxation-dependent differences of the measured values (during measurement the actual measured values abandoned for determination of the relaxation curve, and average values are used instead) become smaller and smaller so that there is the danger, on account of measuring inaccuracies, of a falsification of the determination. One therefore waits until it can be assumed that the relaxation curve has run down by a value that can be determined with sufficient accuracy. The next support point is not provided until this point in time.

Preferably, support points are not determined as long as a change of the internal pressure is being recognized. This can be the case, for example, if at least one average value shows a curve with a slope that exceeds a predetermined measure. It is to be assumed in such ramp sections that the changes in the measured values and/or the average values caused by the relaxation behavior of the vessel are overlaid by changes caused by the internal pressure. Since a clean separation of these two influencing factors is as a rule not possible, or is possible only with difficulty, no support points are formed during these time periods.

The relaxation curve is preferably predicted using the support points in conjunction with a non-linear optimization method. Such methods are known. For example, the evolution strategy, simulated annealing, thresholding accept, random cost method and self-adapted annealing can be used. These methods permit a prediction to be made for the near future from the recent past.

The prediction is preferably made support-point-controlled in the initialization phase and time-controlled in the measuring phase. This achieves a relatively rapid prediction in the initialization phase. In the measuring phase the prediction is repeated according to predetermined time intervals. This is as a rule sufficient. However, it can occur that successive predictions are based on the same support points because no new support point had been established in the interim.

A predetermined number of the last-determined support points is preferably used for the if optimization. Thus, e.g., values determined at the last twenty support points are always used. Values belonging to previous support points can as a rule be rejected because their influence on the prediction for the near future is too small.

The relaxation curve is preferably predicted using the support points with the aid of a mathematical model of the tube, e.g., an Abel kernel. The optimization then becomes simpler and more reliable.

The invention is described in the following using a preferred embodiment in combination with the drawings.

Figure 5:
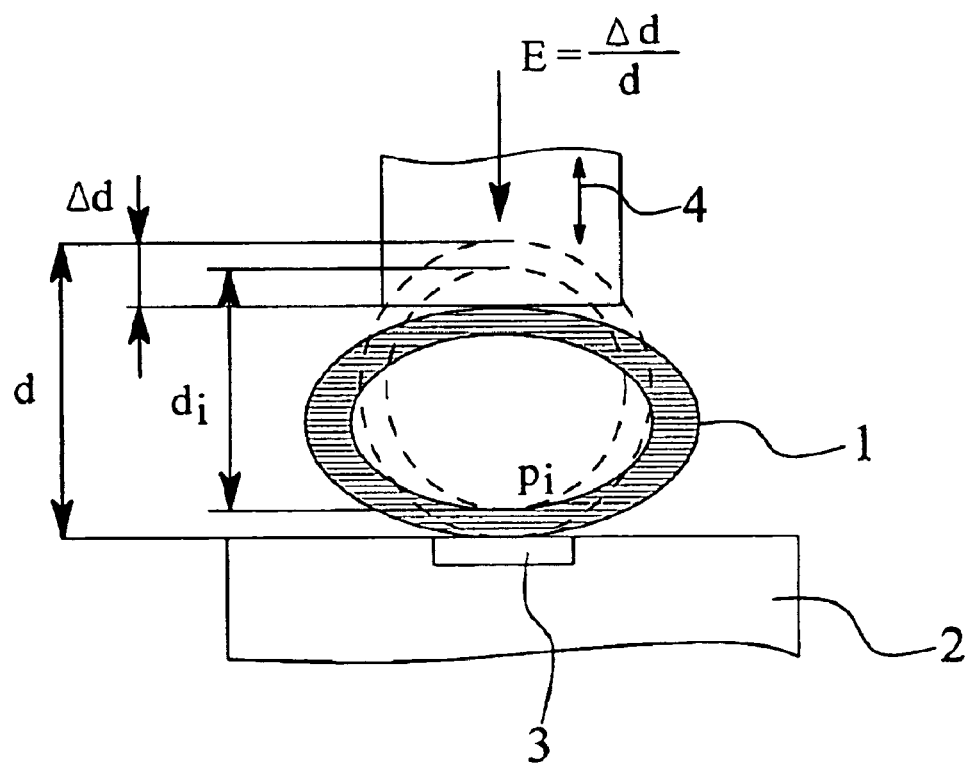
FIG. 5 shows a schematic view of a measuring arrangement.

A device schematically shown in FIG. 5 is used for the non-invasive measurement of tube pressure, that is, for the non-invasive determination of permanent internal pressure in elastic vessels such as tubes, hoses, etc. Details for this are described in DE 197 47 254 A1. The determination of internal pressure takes place by means of a force or pressure measurement at the outer wall of vessel 1. The term "non-invasive" signifies here that the vessel surface must not be changed, nor is communication necessary between the vessel interior and the measurement sensory mechanism, e.g., in the form of a T-branch. Media to be transported can be liquids and gases, generally fluids. Roller pumps, peristaltic pumps or centrifugal pumps can, for example, be used as means for producing the pressure. The measuring principle can be used wherever a communication or contact between the transported fluid and the suroundings is undesired or dangerous. Especially preferred areas of application are tubes where a contamination of the fluid and/or the danger of infection from the outside world, e.g., from attending medical personnel, is/are to be excluded. The measuring method can be used, e.g., in hemodialysis, infusion technology, heart-lung machines, food technology or general engineering.

As an example of the vessel, tube 1 is used, which is shown in a non-deformed state with dashed lines and in a deformed state thickly extended and shaded. Tube 1 rests on support 2 that comprises force sensor 3 in the area of contact with tube 1. Plunger 4 acts on tube 1 and deforms it in that the stamp is moved over distance $\Delta d$ in the direction of support 2. The starting point for distance $\Delta d$ is outer diameter d of tube 1 in its non-deformed state. The advance movement of plunger 4 can be standardized to $$\varepsilon = \frac{\Delta d}{d}.$$

A pressure Pi prevails in tube 1.

The combination of internal pressure Pi with the deformation of tube 1 by plunger 4 results in a force or a reaction force that can be determined at force sensor 3. It is of course also possible to house the force sensor in the front surface of plunger 4. The advance movement ε is shown exaggeratedly large here. Basically, only a movement is required that is sufficient to produce a measurable force on sensor 3 given the pressures Pi occurring in the interior of tube 1.

Figure 1:
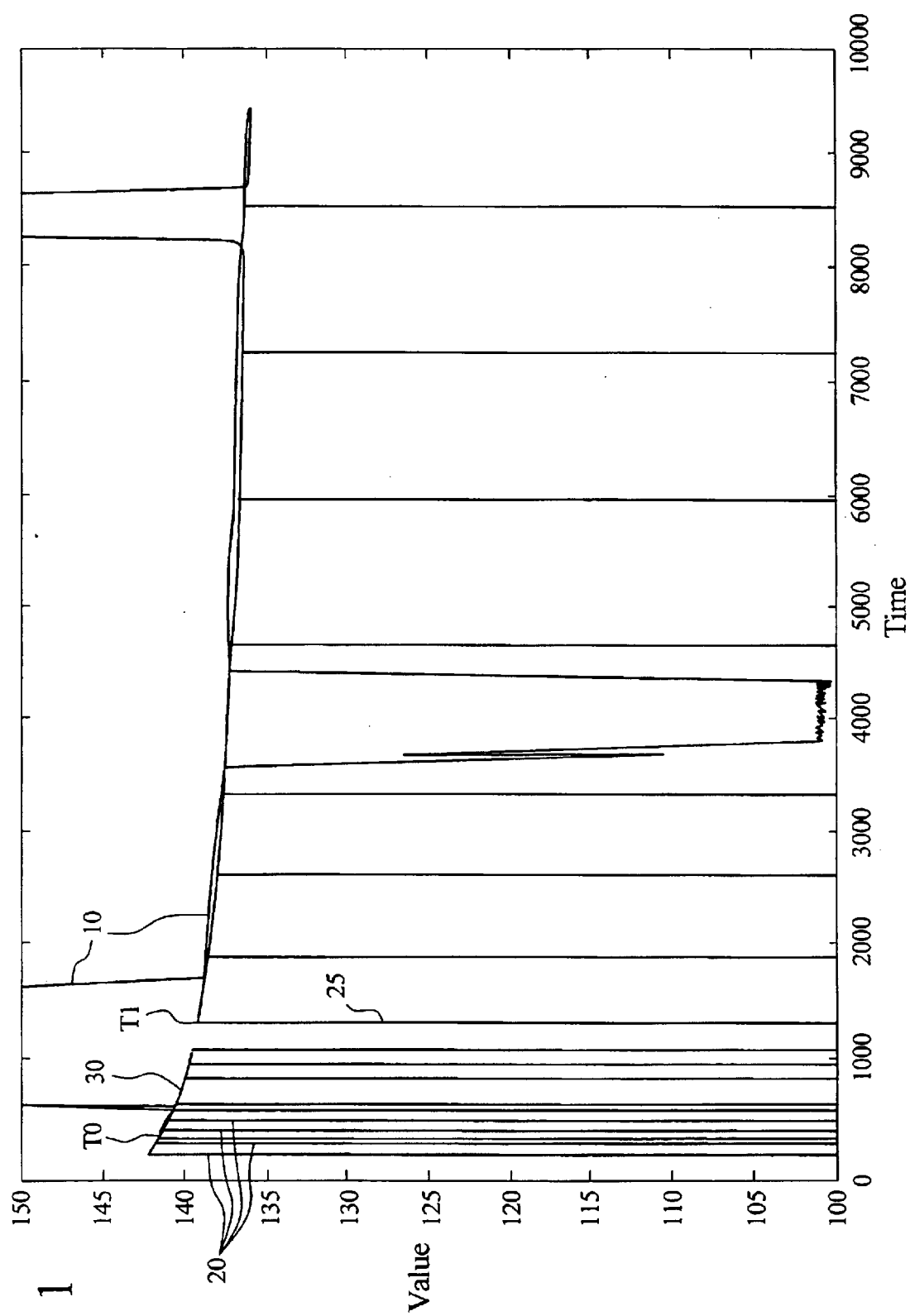
FIG. 1 shows a relaxation curve with support points and pressure jumps.

FIG. 1 shows with a relatively thick line 10 the force values determined by sensor 3. In order to be able to follow these force values even if internal pressure Pi pulses, the average value is formed from the measured force values, that is, starting from the current point in time the individual force values are summed up over a previously established time period in the past and divided by the time period. A relatively smooth curve 10 accordingly results even in the case of a pulsing internal pressure, whose pulsation amplitude is, however, substantially constant. However, jumps can be recognized in this curve 10, at which jumps the pressure level clearly changes.

It is assumed for the following explanation that a pressure different from atmospheric pressure is only present during the time regions in which the jumps are recognizable. The remaining change in the average value is caused by the relaxation of tube 1. Determination of the actual pressure is then made with the aid of a difference of the measured force values and the "zero line" formed by the relaxation curve.

In order to determine this curve, that is, the relaxation curve, internal pressure Pi of tube 1 is first set to atmospheric pressure and a predetermined force is produced on sensor 3 by advancing plunger 4, and is measured there. This force is measured at points in time that closely follow each other, at so-called support points 20. For example, four support points can be determined in the initialization phase that precedes the actual measurement. The further relaxation curve, represented by curve 30, can be predicted using the relaxation curve at these four support points 20. Basically, any non-linear optimization method can be used to predict relaxation curve 30. For example, the evolution strategy, simulated annealing, thresholding accept, random-cost method and self-adapted annealing were successfully tested.

As soon as relaxation curve 30 can be predicted, the required difference of the measured values and the predicted relaxation curve can be formed at each point in time.

For reason of clarity, curve 10 of the average values is shown in FIG. 1 somewhat above relaxation curve 30 after point in time 2000 (horizontal axis). However, in reality the two curves 10 and 30 coincide outside of the jumps, and would therefore lie superimposed on one another.

The prediction determined up to point in time T0 is only a rough reproduction of the relaxation curve, which is stabilized at point in time T1.

Further support points 25 are formed even after the start of measurement at point in time T1, and the predicted relaxation curve is checked using these support points.

In this connection, note that the support points in the initialization phase are at fixed points in time. After the initialization phase support points are established only where it can be assumed, based on the predicted relaxation curve, that the relaxation values are different enough at these support points to be measured with sufficient reliability.

It can therefore be recognized that the intervals between individual support points become greater and greater.

Thus, curve 10 is determined at first from the average values over a predetermined time window. A determination is made at support points 20, 25 from this curve 10. The values at the last twenty support points are then used for the prediction of the relaxation curve or trend. If twenty support points are not present, all past support points are used.

As has already been explained, it is difficult in some instances to recognize whether a change of the measured values recorded by sensor 3 is due to a change of internal pressure Pi or to the relaxation behavior of tube 1.

Figure 2:
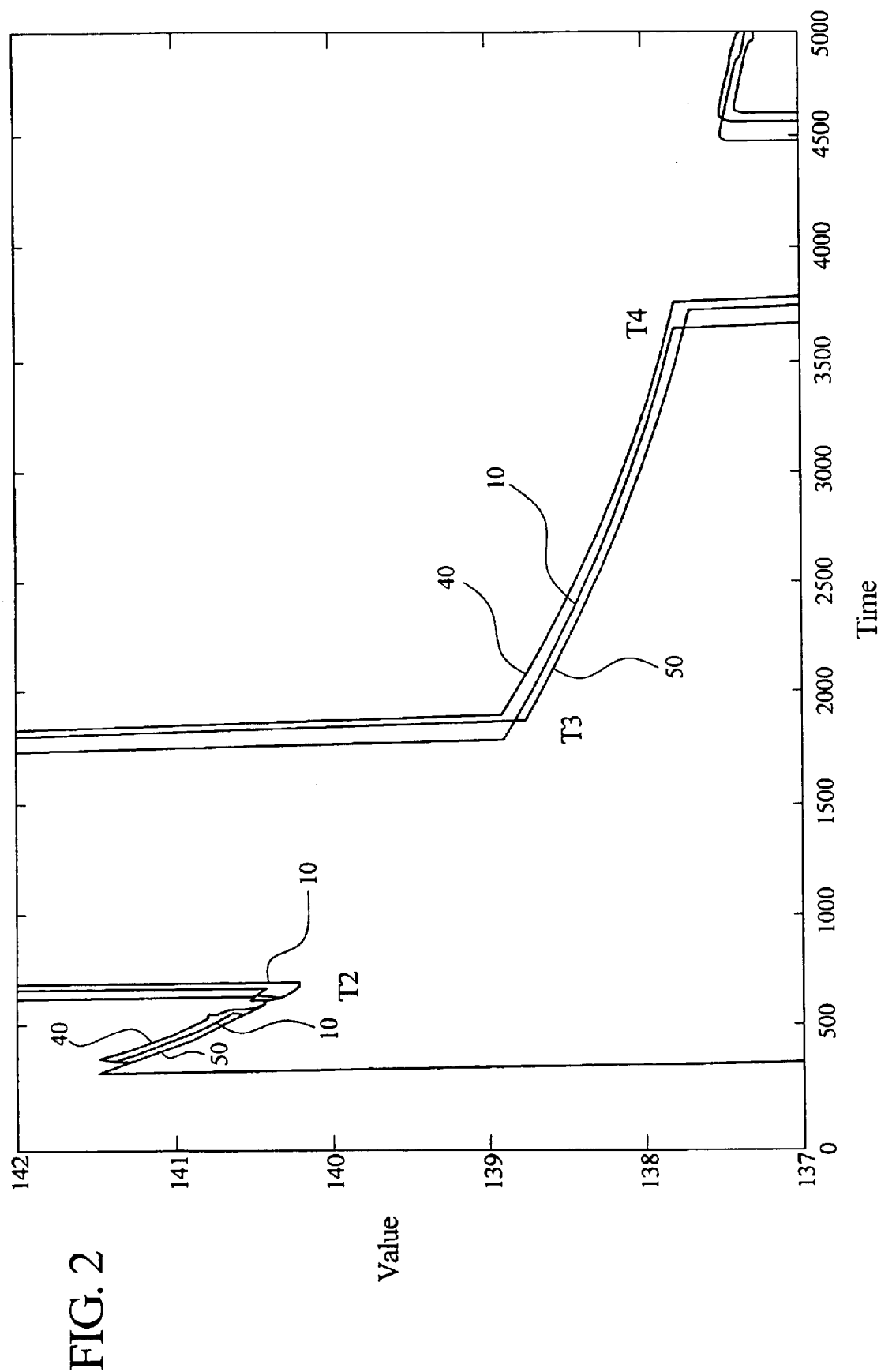
FIG. 2 shows an enlarged section of the curve of FIG. 1.

One possibility of making a decision about this is disclosed in FIG. 2. FIG. 2 shows an enlarged section from FIG. 1. Line 10 representing the average values is sketched in here. The average values are also designated as moving average value or sliding average value because these average values are always averaged back over a time window of predetermined length into the past.

Two limits are now formed that are represented by lines, 40, 50. The first limit 40 is based on the fact that the relaxation curve falls monotonically. Every rise of average values 10 can therefore not be due to the relaxation, but rather must be based on a change of internal pressure. Naturally, a certain distance is to be observed here, because the average values have a certain spread caused by measuring inaccuracies.

The other limit 50 is fixed based on the premise that the amount of the slope of the relaxation curve always decreases. The gradient thus becomes less and less over the course of time. If the average values 10 diminish more than limit 50 permits, a change of the internal pressure Pi is also present. It can be recognized in FIG. 2 that curve 10 of the average values has left the region between the two limits 40, 50 at point in time T2. This must then be due to a pressure jump. At a point in time T3 curve 10 of the average values enters back into the region between the two limits 40, 50. After this point in time T3 it can be assumed to a good approximation that changes in average values 10 are caused by the relaxation of tube 1. At a point in time T4 a pressure jump occurs again that is determined from the fact that curve 10 leaves the region between limits 40, 50.

However, not only jumps can be determined with this checking possibility, but also slow changes in pressure that can result, e.g., if an infusion needle becomes clogged over the course of time.

Figure 3:
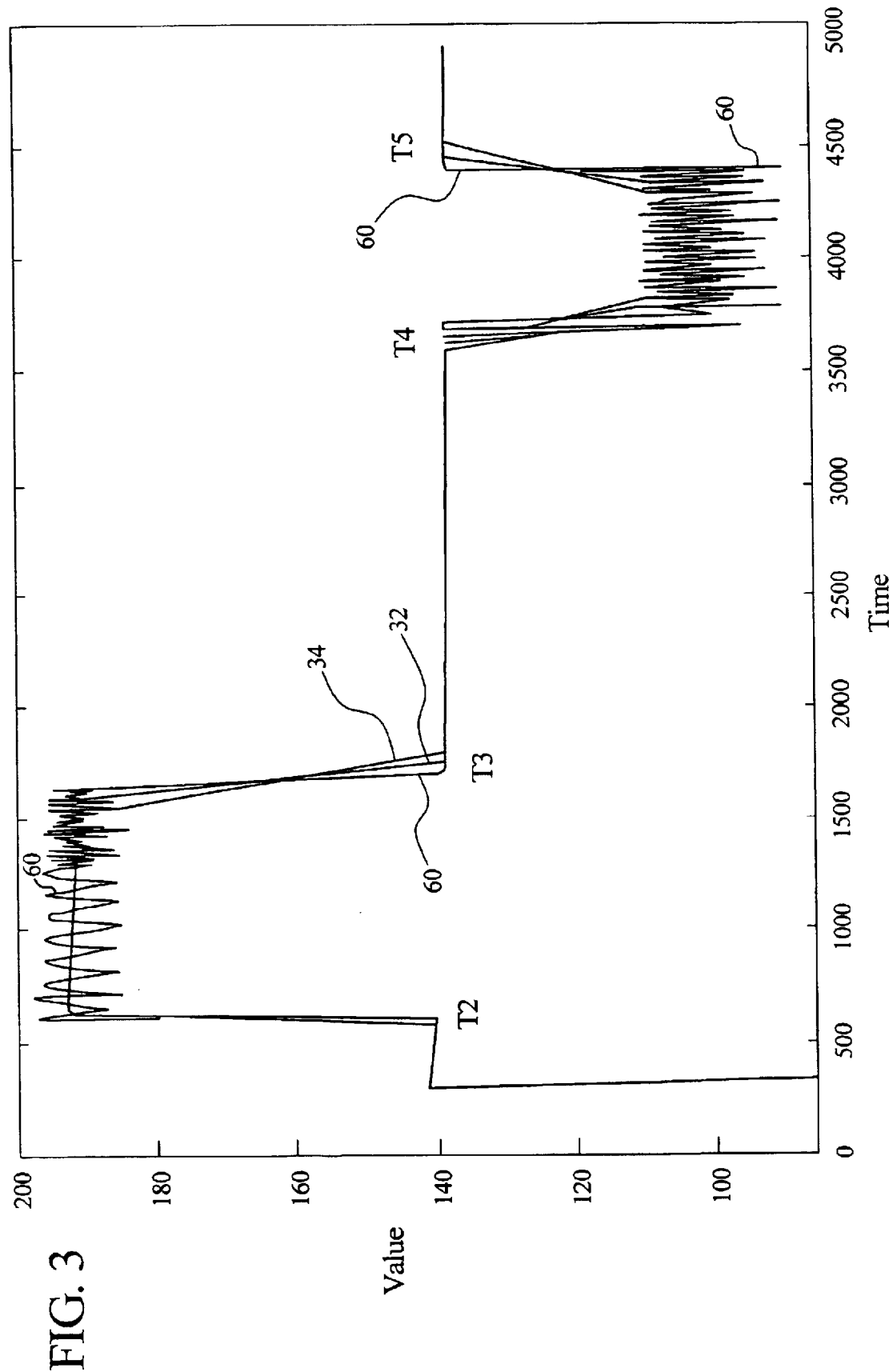
FIG. 3 shows a curve of measured values with jumps.
Figure 4:
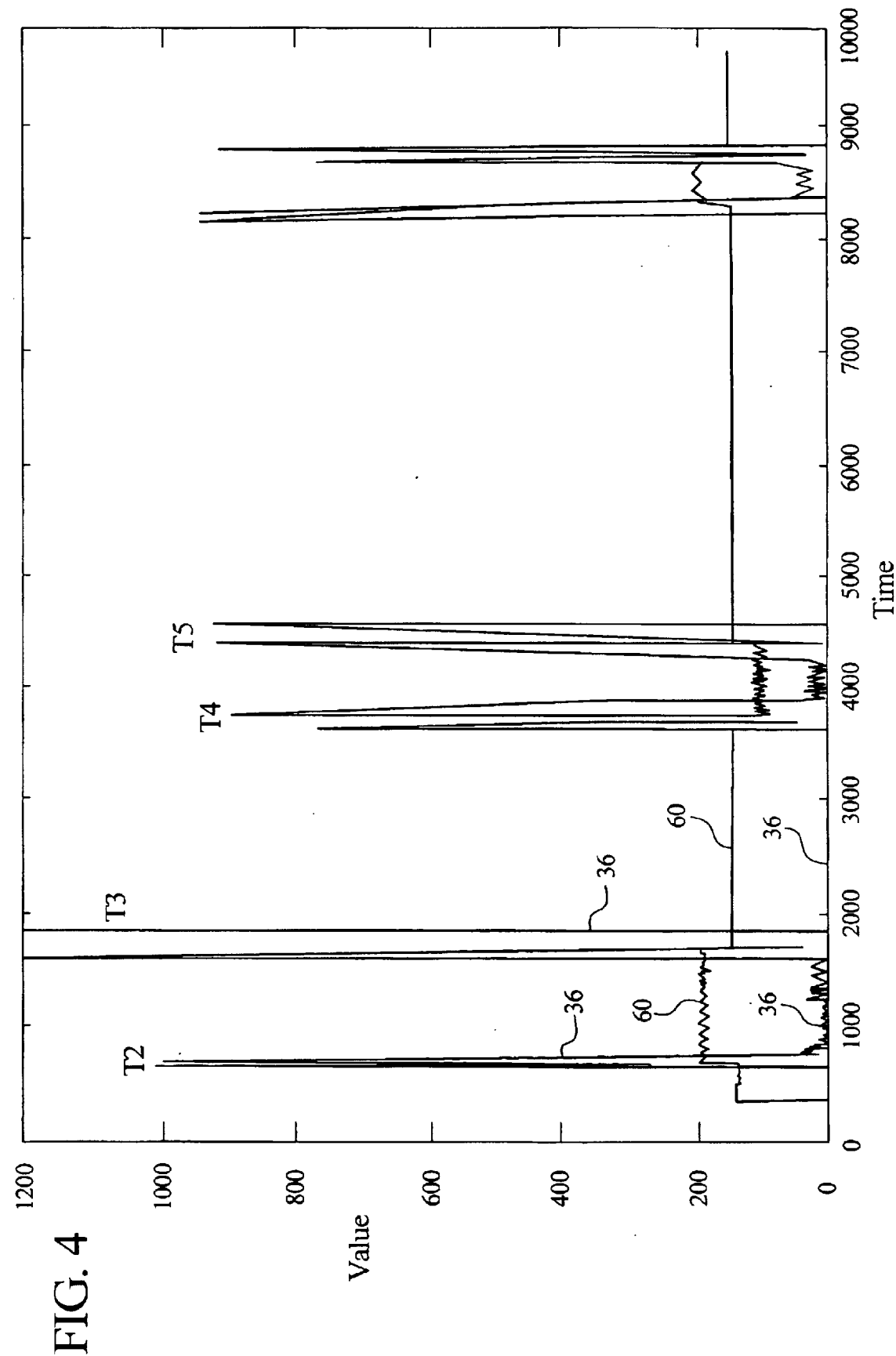
FIG. 4 shows a view of the differences of average values with different smoothing widths.

FIGS. 3 and 4 show another possibility of discovering jumps in the pressure curve. The jumps are an especially critical criterion.

FIG. 3 shows a curve 60 of the measured values, that is, of the force values actually determined at sensor 3. It can be recognized that the force between points in time T2 and T3 jumps positively to a higher amplitude and oscillates there, whereas it jumps to a negative value, relative to the predicted relaxation, between points in time T4 and T5.

Two average values 32, 34 are now formed. The average value 32 is formed, e.g., over the last fifty sensed values, and average value 34 over the last one hundred sensed values. Both average values 32, 34 are of course continuously formed and updated at each new sensed value. Accordingly, average value 32, which has a lesser smoothing width than average value 34, reacts more rapidly to changes in measuring signal 60 than does average value 34. This is already clearly recognizable in FIG. 3. However, the situation becomes even clearer if FIG. 4 is examined. The difference between the average values is plotted as a curve 36 in FIG. 4. In addition, curve 60 of the measured signals is sketched in.

It can be clearly recognized that curve 36 of the differences between average values 32,34 is normally in the vicinity of the zero line. Difference 36 also pulses where measured signals 60 pulse, that is, between points in time T2, T3 and T4, T5.

However, differences 36 rise quite sharply at points in time T2–T5, so that jumps of internal pressure Pi are clearly recognizable.

Thus, in order to evaluate the measured values from sensor 3, relaxation curve 30 is first of all predicted. The information necessary for this is obtained from the values at support points 20 in the initialization phase. If a jump occurs, the measured amplitude is reduced by the predicted value of the relaxation curve. The actual internal pressure value can then be calculated from this difference. As can be recognized from FIG. 3, even the elevated measured values between points in times T2, T3 are subject to a certain reduction that is due to the relaxation. Since the "jump height" is known at the beginning, further support points 25 (FIG. 1) can also be used now in order to predict relaxation curve 30 anew. To this end the values determined, e.g., at the last twenty support points, are filed in a shift register and these twenty values are used in one of the above-named, non-linear optimization methods to predict relaxation curve 30 or the trend for the near future. Since the relaxation curve can be continuously checked and corrected in this manner, a reliable measurement result that takes into account the relaxation of tube 1 is always obtained even in the case of rather long-lasting measurements.

The method can therefore be briefly summarized as follows:

Measurement signals are continuously picked up and support points are stored. Ramps and creeping pressure rises are determined with the aid of the average values and/or of the slope triangle. With the aid of a non-linear optimization method, the mathematical model is adapted to the prediction of the relaxation using the last support points. The adaptation is cyclically repeated and improved. Support points are not generated if internal pressure changes are recognized, e.g., during the time periods in which ramps or creeping pressure changes are detected. The internal pressure is determined from the difference between the measurement signals and the predicted relaxation.

The procedure described can be deviated from in many respects without departing from the core concept of the invention.

For example, the optimization can always be started in a time-controlled manner, during which the time intervals between the individual support points differ. The first two optimizations are then performed with very short intervals in order to make possible a rapid start of measurement. This means very small time intervals between the support points in order to always have partly old and partly new values available within a shift register for adaptation of the model. Although different time intervals are not a general prerequisite for the method they are useful because they make an earlier start of measurement possible.

It is also not a mandatory requirement to determine the support points in a time-controlled manner and to start the adaptation in a time-controlled manner. It must merely be ensured that the checking or adaptation of the relaxation curve is improved from time to time, and that new support are inserted. However, the mixed procedure, that is, time-controlled on the one hand and support-controlled on the other hand, is advantageous for a few applications.

What is claimed is:

1. A method for noninvasive measurement of an internal pressure in elastic vessels in which a force is measured on the outer surface of the vessel and the internal pressure is ascertained with the aid of a difference from the measured force and a relaxation profile estimated in advance, characterized in that the relaxation profile is repeatedly checked after the start of the measurement.

2. The method according to claim 1, characterized in that the relaxation profile is ascertained with the aid of an averaging method.

3. The method according to claim 2, characterized in that an averaging is done in at least two different ways which differ in their smoothing width.

4. The method according to claim 3, characterized in that a difference of the averages is continuously formed with differing smoothing widths.

5. The method according to claim 2, characterized in that a periodicity of the measured force is ascertained and a window width of the averaging method is matched to the periodicity at least from time to time.

6. The method according to claim 1, characterized in that a first limit is continually formed, resulting from the fact that the relaxation profile decreases monotonically, and a second limit, resulting from the fact that a slope of the relaxation profile decreases, and a change of the internal pressure is recognized when the relaxation profile exceeds one of the two limits.

7. The method according to claim 1, characterized in that support points are repeatedly determined in order to predict the relaxation profile.

8. The method according to claim 7, characterized in that the support points are determined at predetermined points in time in an initialization phase and, in a measurement phase, after a predetermined change of the predicted relaxation profile.

9. The method according to claim 7, characterized in that the support points are not ascertained as long as a change of the internal pressure is recognized.

10. The method according to claim 7, characterized in that the relaxation profile is predicted using the support points and a nonlinear optimization method.

11. The method according to claim 8, characterized in that the prediction is support-point-controlled in the initialization phase and time-controlled in the measurement phase.

12. The method according to claim 7, characterized in that a predetermined number of the most recently ascertained support points are used for optimization.

13. The method according to claim 7, characterized in that the relaxation profile is predicted using the support points with the aid of a mathematical model of the vessel.

* * * * *